United States Patent [19]

Bahner et al.

[11] 4,358,208

[45] Nov. 9, 1982

[54] APPARATUS FOR DETERMINING ENTHALPY OF A FLUID MEDIUM

[75] Inventors: Friedrich Bahner, Rotenburg; Harry Pleva, Horb, both of Fed. Rep. of Germany

[73] Assignee: Babcock-BSH Aktiengesellschaft, Krefeld, Fed. Rep. of Germany

[21] Appl. No.: 107,654

[22] Filed: Dec. 27, 1979

[30] Foreign Application Priority Data

Dec. 27, 1978 [DE] Fed. Rep. of Germany ....... 2856288

[51] Int. Cl.³ .................. G01K 17/16; G01K 3/00
[52] U.S. Cl. ..................................... 374/41; 374/112
[58] Field of Search .............. 73/344, 190 R, 190 H, 73/193, 861.35, 204

[56] References Cited

U.S. PATENT DOCUMENTS

| | | | |
|---|---|---|---|
| 1,691,600 | 11/1928 | Brush, Jr. et al. | 73/204 |
| 2,193,762 | 3/1940 | Hirsch et al. | 73/204 |
| 2,728,225 | 12/1955 | Skibitzke | 73/204 |
| 3,204,447 | 9/1965 | Krause et al. | 73/190 R X |
| 3,422,675 | 1/1969 | Shannon et al. | 73/190 R |
| 3,459,040 | 8/1969 | Halbach | 73/190 R |
| 3,498,126 | 3/1970 | Vassallo | 73/190 H X |
| 3,596,516 | 8/1971 | Haynes, Jr. | 73/190 R |
| 3,605,490 | 9/1971 | Progelhof et al. | 73/190 H |
| 3,618,360 | 11/1971 | Curtis | 73/861.35 |

FOREIGN PATENT DOCUMENTS

| | | | |
|---|---|---|---|
| 2263754 | 12/1972 | Fed. Rep. of Germany | 73/192 |
| 2235853 | 3/1976 | Fed. Rep. of Germany | 73/204 |
| 201694 | 11/1967 | U.S.S.R. | 73/204 |

Primary Examiner—Daniel M. Yasich
Attorney, Agent, or Firm—Michael J. Striker

[57] ABSTRACT

Enthalpy quantities such as the degree of moisture of gases, the wetness of steam or the enthalpy of dry steam are measured by passing a specific amount or dosage of a gas or steam through a system such as a cooler or dryer wherein its thermal condition is changed while measuring the inlet and outlet temperature, and measuring heat radiated into the condition changing system whereupon the desired enthalpy quantity is obtained from a heat balance equation set up from the measured and known data.

9 Claims, 3 Drawing Figures

APPARATUS FOR DETERMINING ENTHALPY OF A FLUID MEDIUM

BACKGROUND OF THE INVENTION

The invention relates to a process and apparatus for determining quantities relevant to enthalpy of a gaseous medium, such as degree of moisture in gases, vapor humidity or enthalpy of dry steam.

A similar process has been described in German Pat. No. 2,235,853. With this known process the gas flow to be measured is cooled below the dew point by means of a continuously operating countercurrent cooling device. The heat exchange with the cooling device is measured and the temperature of the gas flow is determined prior to and after the cooling operation and the moisture contents is found via the heat balance equation. The apparatus used in this process is provided with a pump which sucks the gas flow through the countercurrent cooler. A second pump which is operated together with the first pump by a motor drives the flow of the cooling agent through the cooling device. Temperature sensors are provided to measure the temperature, the inlet and the outlet temperature for the gas and the inlet and outlet temperature of the cooling water. The data thus obtained are passed into a computer where the results are produced by virtue of the heat balance equation.

A shortcoming of this process and device is that in order to measure the heat released to the system for changing the physical condition, that is the cooling device, it is always necessary to maintain a flow of cooling medium. Any device of this kind can therefore be only used as a stationary apparatus.

An object of the present invention is to simplify prior art devices of this kind and to permit a broader use thereof.

ESSENCE OF THE INVENTION

This is accomplished in the present process by measuring the heat which is released or absorbed in the condition modifying system as determined by a heat flow measuring device.

Thus, a specific amount or specific dosage of a gaseous or vaporous medium is passed through a system for changing its thermal condition. The entry and outlet temperature of the gas when passing through this system is measured. The system may be a cooling or heating device. The heat absorbed or released by the condition modifying system is furthermore measured and the amount of enthalpy is then determined from a heat balance equation.

More specifically, air humidity may be measured by the process of the invention by passing the gas through a series connection of an inlet duct provided with a dosage nozzle, a mass flow measuring device and a heat flow measuring device which is associated with a cooling device and, if desired, a supplemental cooling device and an outlet temperature measuring device. The mass flow meter consists of an inlet temperature measuring device and a heat flow element with an associated heating as well as an outlet temperature measuring device.

By minor modification of the arrangement of these basis elements a device can be obtained for measuring himidity of a vapor. Moist steam of which the temperature is measured in a steam space is in this case passed through a heat flow measuring device in which centrally or concentrically a heater is provided. The "dry" steam is then removed by suction through a temperature measuring chamber and a dosage nozzle and/or a heat flow meter as described above. A device for enthalpy determination is obtained if steam from the steam chambers passes by way of a dosage device into a heat flow measuring device which is provided with a cooling apparatus. The steam thus is subject to condensation and the temperature of the condensate is measured. There may further be included a device for maintaining a constant level of the condensate.

The evaluation of the ascertained individual data can be effected in conventional manner by means of a suitable electronic computer data processing which is programmed for solving a specific heat balance equation set up according to the particular measuring apparatus.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

PREFERRED EMBODIMENTS OF THE INVENTION

Figure 1:
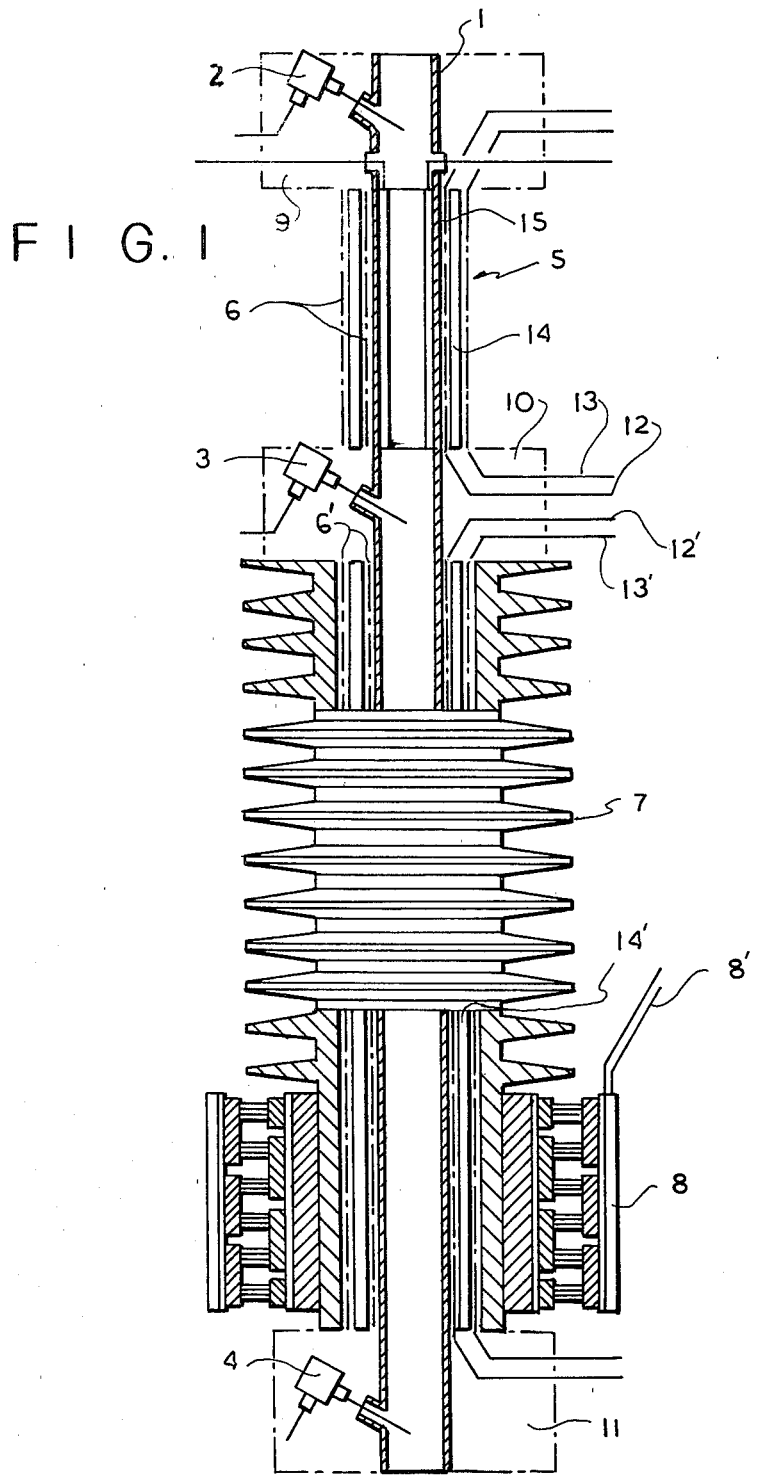
FIG. 1 is a vertical section through an air humidity measuring apparatus provided with a built-in heat flow measuring device.

In the following discussion the subsequent nomenclature will be used:

N = heating power or wattage
k = proportionality factor
m = mass flow
c = specific heat
$\theta_1$ = inlet temperature
$\theta_2$ = outlet temperature
$\Delta\theta$ = temperature difference
$m_f$ = total mass flow
x = steam humidity
r = evaporation heat
$c_D$ = specific heat of steam
h = enthalpy of steam
$c_W$ = specific heat of water
h" = evaporation heat
$q_u$ = heat caused by super heating The air humidity measuring apparatus shown in FIG. 1.

The air humidity measuring apparatus shown in FIG. 1 comprises an elongated tube 1 of a suitable material such as a corrosion-resistant metal. Temperature sensors 2. 3 and 4 pass through the walls of the tube into the interior and thus enter the gas flow to be measured which passes through the tube. At the upper end of the tube 1 there is provided a mass flow meter 5 which in this case is in the form of a thermal-type mass flow meter which includes a heat flow meter 6.

The measurement of the mass flow could also be effected by a conventional measuring process, for instance by a differential pressure measurement or it could be dispensed with entirely if provision is made that the mass flow is maintained at a constant level, for instance by means of a dosage device.

The tube 1 is surrounded by a cooling system 7 and 8 which is integrally connected with a heat flow meter 6'. In the drawing are shown by way of example cooling ribs of an aircooler 7 and Peltier elements of a Peltier cooler 8.

The tube 1 is surrounded at its ends, that is outside the parts 5 to 8, with heat insulating sheaths 9, 10 and 11. Through these sheaths electric connections are passed for the temperature sensors 2, 3 and 4 and the heat flow meters 6 and 6'.

The heat flow meters 6 and 6' consist of electrically insulated wire coils 12, 13 and 12', 13' which are concentrically wound around the tube 1 and consist of temperature dependent resistance material. Between the wire coils 12 and 13 of meter 6, and coils 12' and 13' of meter 6' there is provided a layer 14 and 14', respectively, which has a moderate thermal conductivity and a definite thickness and which will be called a "heat resistance". The mass flow meter 5 furthermore contains an electric heater 15 which is provided in the interior of the tube 1. The heater is supplied with current through connections which extend through the walls of the tube 1 and the heat insulating covers or sheaths 9.

The outlet terminals of the temperature sensors 2, 3 and 4 and the terminals of the coils 12, 13 and 12', 13' of the heat flow meters 6 and 6' are connected to an electronic computer (not shown) which is set up to solve a heat balance equation from known and measured data.

The connections 8' of the Peltier cooler 8 are connected also with a suitable source of electric power.

The operation of this device is as follows:

By means of the temperature sensor 2 the inlet temperature $\sigma_1$ of the gas to be measured is ascertained. The heat flow through the walls of the tube 1 causes at both sides of the heat resistance layer 14, that is in the coils 12 and 13, a temperature difference $\Delta\theta$ which in turn causes different resistance changes in respective coils 12 and 13, and the heat flow value thus can be determined. Together with the outlet temperature $\theta_2$ which is measured by means of the sensor 3, the mass flow m can be found by means of a heat balance equation.

$$\dot{m} = \frac{N - k \cdot \Delta\theta}{c(\theta_2 - \theta_1)}$$

In this equation N denotes heating power or wattage of the heater 15, k is an apparatus constant and c denotes specific heat of the gas to be measured. c is known only approximately since it depends on the humidity value which is to be found. Likewise m includes a degree of humidity since $\dot{m} = \dot{m}_L(1+x_1)$. In this latter equation $x_1$ denotes the humidity degree at the inlet which is to be determined and $\dot{m}_L$ denotes the dry mass flow. The solution of the equation $\dot{m} = m_L(1+x_1)$ must therefore be obtained by means of iteration since initially specific heat of the dry air $c_L$ is used and it is assumed that $\dot{m} = \dot{m}_L$, whereupon absolute humidity is determined by means of an equation given below and thereafter all calculations have to be repeated.

The gas being measured is then passed through the cooling system 7, 8 and in doing so it radiates heat. The heat flow released through this cooling system is measured by the heat flow measuring device 6" which includes the coils 12', 13' and the heat resistance 14'. The device 6' measures the heat flow in the same manner as above in connection with device 6 described. If the thus measured temperature difference is $\Delta\theta_o'$, then the heat amount which is radiated into the cooling device 7 and measured by the heat flow measuring device 6' equals $k_o \cdot \Delta\theta_o'$, in which case $k_o$ is again a constant of the apparatus.

By means of the temperature sensor 4 the air temperature $\theta_3$ is measured at the outlet. The cooling action is effected in such a manner that the air at the outlet of tube 1 is saturated with water. The humidity value $x_1$ which is to be measured at the input of the measuring apparatus is obtained by setting up and solving the following heat balance equation:

$$k_o \cdot \Delta\theta_o + (x_2 - x_3)\theta_3 \cdot \dot{m}_L = \dot{m}_L \cdot \{c_D(\theta_2 - \theta_3) + r_o(x_1 - x_3) + C_D \cdot (x_1\theta_2 - x_3\theta_3)\}$$

The nomenclature herein used has been given before. In addition, $k_o \cdot \Delta\theta_o$ denotes heat power determined by the heat flow meter 6' and into the cooling system 7, 8. $(x_2 - x_3)\theta_3 \cdot \dot{m}_L$ denotes the heat quantity radiated by the condensate. The right hand side of the equation is the enthalpy difference between inlet air and outlet air.

The calculation of humidity value, from the above equation can be carried out automatically by a date processing computer. The data $\theta_1$, $\theta_2$, $\theta_3$, $\Delta\theta$ and $\Delta\theta_o$ are automatically read, registered and processed in the computer.

Figure 2:
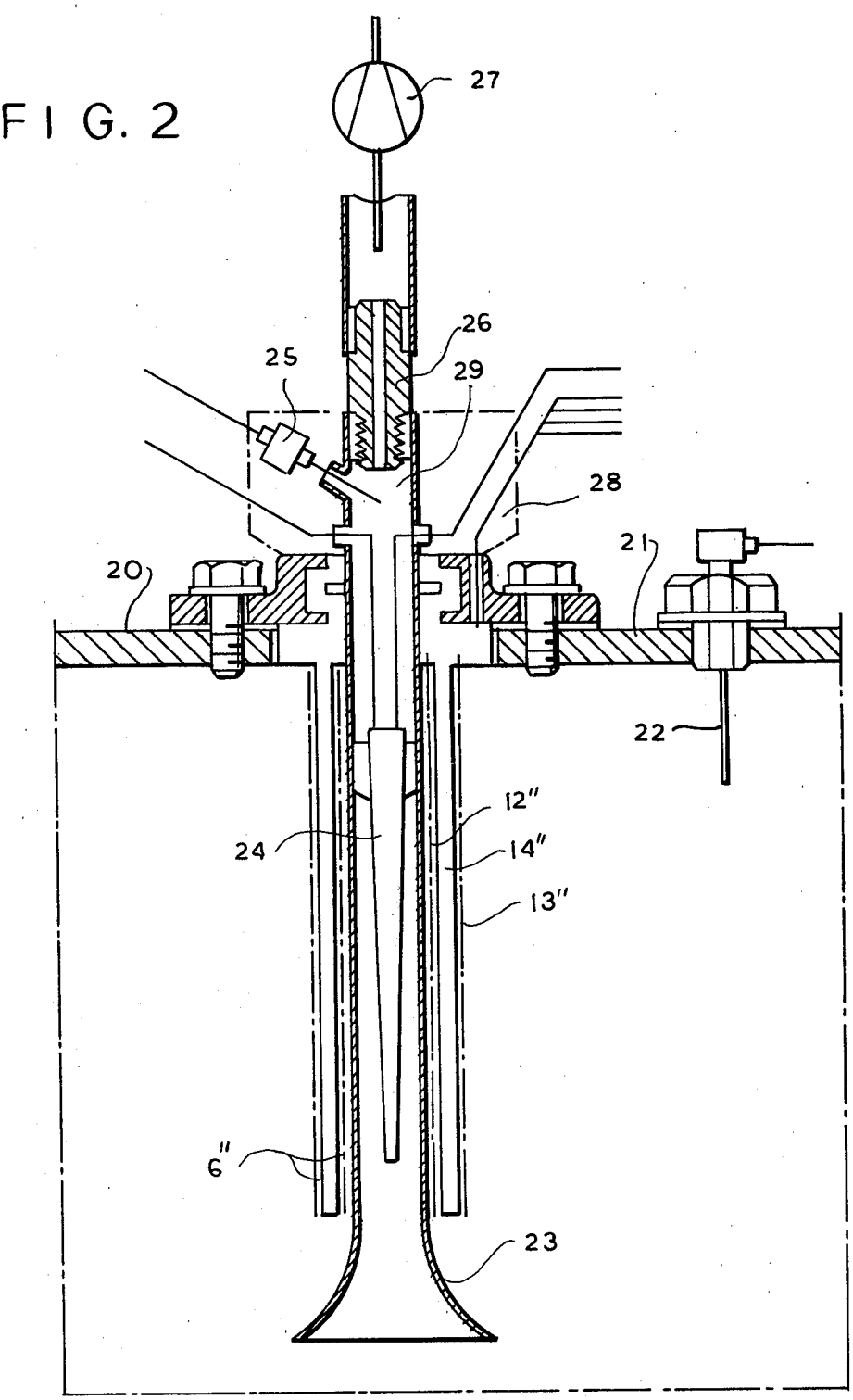
FIG. 2 is a vertical section through a steam humidity measuring device according to the invention.

FIG. 2 illustrates an apparatus for measuring moisture contents of a steam. In this figure reference 20 indicates a steam space or a steam chamber. A temperature sensor 22 and a heat flow measuring device 6" pass through the wall 21 and extend into the steam chamber 20. The heat flow measuring device 6" is built in the same way as the device 6 described in FIG. 1.

Numerals 12" and 13" indicates the corresponding coils and reference numeral 14" indicates the corresponding heat resistance layer. The heat flow measuring device 6" peripherally surrounds a tube 23 which in its interior includes an electric heater 24 which may, for instance, have a conical form. A further temperature sensor 25 enters the tube above the heated portion. The tube 23 finally terminates in a device for keeping the measured amount of steam constant. This device in the present case is in form of a turbulence nozzle 26 and a vacuum pump 27.

In lieu of the last mentioned parts it would also be possible to employ a thermal type mass flow measuring device as described in connection with FIG. 1. Reference numeral 28 indicates a heat reducing sheath. All parts of the apparatus are removably secured in the wall 21. The fastening means are in the form of screw connections with the necessary seals. Besides, all of the measuring devices are again connected with a suitable computer which is not shown in the Figure.

The operation of this device is an follows:

The wet steam after determinging its inlet temperature ($\theta_1$) by means of the temperature sensor 22 enters the heat flow measuring device 6". By this device there is again measured the temperature difference $\Delta\theta$ which is caused by the heat flow. The steam is then dried by means of the heater 24. It then enters in superheated condition into the temperature measuring chamber 29 in which by means of the sensors 25, the outlet temperature $\theta_2$ of the superheated steam is measured.

To obtain the wetness value of the steam a heat balance equation must be set up. The constant heat power N of the heater 24 is used up by heat losses ascertained by the heat flow measuring device), by evaporation heat used for evaporation of water drops, and by the heat employed for superheating the steam. The heat balance equation therefore reads as follows:

$$N = k \cdot \Delta\theta + \dot{m}_f \{(1-x) \cdot r + c_D(\theta_2 - \theta_1)\}$$

In this equation only the steam wetness value x is unknown. Evaporation heat r and specific heat $c_D$ of steam can be obtained from tables. N is a constant heating power. is the temperature difference obtained in the heat flow measuring device with the apparatus constant k. $\theta_1$ is the inlet temperature of the wet steam and $\theta_2$ is the outlet temperature of the superheated steam.

Figure 3:
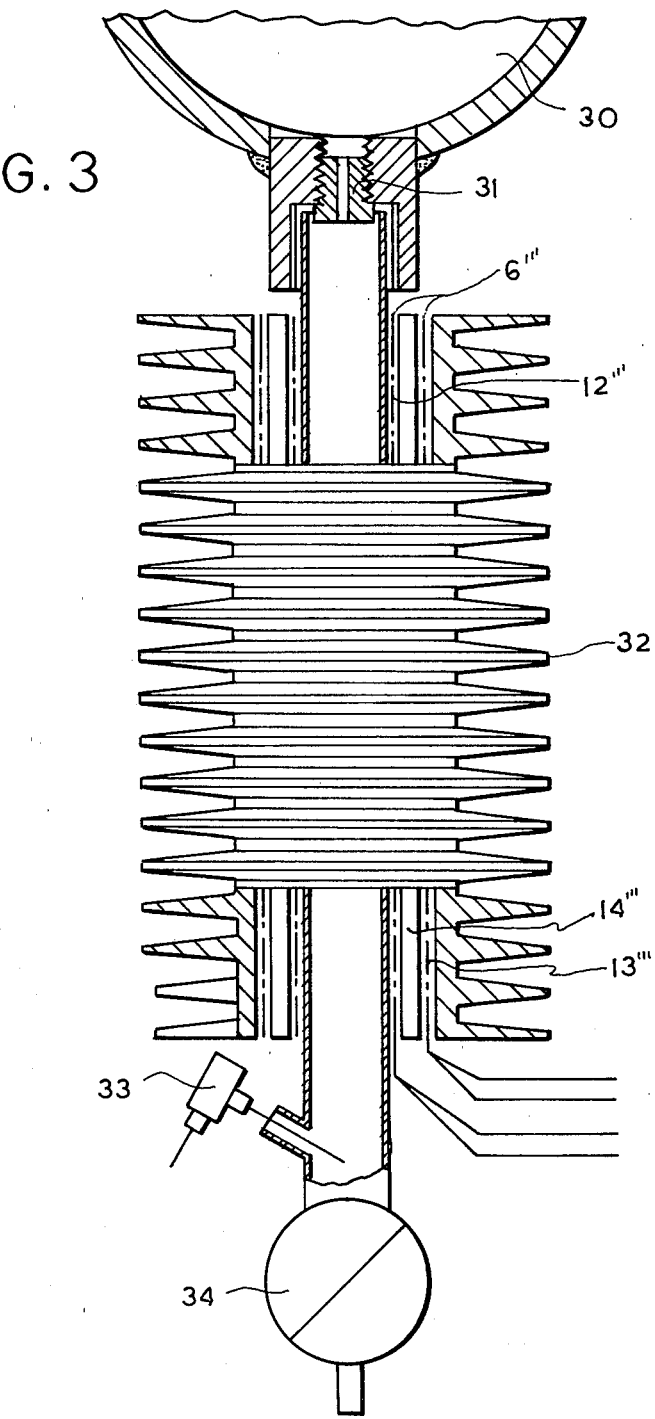
FIG. 3 is a vertical section through a measuring device for determining enthalpy of steam, the measuring device being provided with a built-in heat flow measuring apparatus according to this invention.

In FIG. 3 an apparatus is shown for determining an enthalpy of dry steam.

In this apparatus there is provided a steam space 30 from which a steam having enthalpy $h = h'' + q_u''$ is passed through a dosage nozzle 31 into the heat flow measuring device 6''' which is surrounded by the cooling device 32. This heat flow measuring device 6'''''' has the same structure and the same manner of operation as described in connection with the previous Figures. Into the cooling device 32 a heat amount N is transferred and the steam leaves the cooling device 32 in the form of a condensate of which the temperature is measured by means of the temperature sensor 33. A condensate collector 34 is provided downstream of the cooling device 32. All of the temperature measuring devices are again connected with an electronic computer programmed so as to solve the heat balance equation.

In the case of this embodiment the heat balance equation is as follows:

$$\dot{m} \cdot h = N + \dot{m} \cdot c_W.$$

$$h = N + c_W.$$

Reference is made in this connection also to the above given nomenclature.

The mass flow in of the steam can be determined in different ways. For instance follinging the dosage nozzle 31 there may be provided a thermal-type mass flow meter as described in FIG. 1. Since the critical pressure ratio is exceeded in most uses of the device, the flow depends only on the steam pressure upstream of the dosage nozzle 31. It is therefore the simplest way to ascertain the through flow from the steam pressure.

The reference to thermal or temperature dependent resistance in the above description always refers to a material having a temperature coefficient which is proportional to electrical conductivity.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by the Letters Patent is set forth in the appended claims:

1. An apparatus for determining quantities of enthalpy of a fluid medium, comprising tubular duct means through which the medium is passed; means for measuring mass flow of the passing medium; a system for altering thermal condition of the passing medium so as to cause the medium to release or absorb heat; means for measuring inlet and outlet temperatures of the passing medium; heat flow measuring means installed between said duct means and said thermal condition altering system, said heat flow measuring means including two concentric electrically insulated wire coils of a material having temperature dependent resistance, said coils being disposed around said duct means in spaced and concentric relationship to each other, and further including a layer of a material of a moderate thermal conductivity and having a predetermined thickness, said layer being interposed between the two wire coils to form a thermal resistance, and said coils arranged at opposite sides of the thermal resistance to determine the heat flow as a function of temperature difference across said resistance; whereby the quantities of enthalpy are computed from a heat balance equation which is set up from the measured data of mass flow, heat flow and the inlet and outlet temperatures.

2. The apparatus as defined in claim 1, wherein said heat flow measuring means is installed on said thermal condition altering system.

3. The apparatus as defined in claim 2, wherein said means for measuring the mass flow of the passing medium includes a thermal-type heat flow measuring device including two concentric electrically insulated wire coils of a material having temperature dependent resistance, said coils being disposed around said duct in spaced relationship to said thermal condition altering system, and further including a layer interposed between said two wire coils and consisting of a moderate heat conductor of a specific thickness, and further including said temperature measuring means arranged at opposite ends of said duct means.

4. The apparatus as defined in claim 3, wherein said thermal condition altering system is a cooling system including a Peltier cooler.

5. An apparatus for determining wetness of a steam medium, comprising tubular duct means through which the steam medium is passed from a steam chamber; means for controlling mass flow of the passing medium; a heating device associated in said duct means for altering a thermal condition of the passing medium; means for measuring inlet and outlet temperatures of the passing medium; heat flow measuring means being installed around said duct means, said heat flow measuring means including two concentric electrically insulated wire coils of a material having temperature dependent resistance, said coils being disposed around said duct means in spaced and concentric relationship to each other, and further including a layer of a material of a moderate thermal conductivity and having a predetermined thickness, said layer being interposed between the two wire coils to form a thermal resistance, said coils arranged at opposite sides of the thermal resistance to determine the heat flow as a function of temperature difference across said resistance; and a chamber for receiving steam discharged through said duct means whereby the quantities of enthalpy are computed from a heat balance equation which is set up from the measured data of mass flow, heat flow and the inlet and outlet temperatures in said steam and receiving chambers, respectively.

6. The apparatus as defined in claim 5, wherein said heating device is an electrical heater disposed in said tubular duct.

7. The apparatus as defined in claim 6, wherein said electric heater has a conical configuration.

8. The apparatus as defined in claim 5, wherein the means for measuring temperature in said steam chamber and the heat flow measuring means are exchangeably mounted in the wall of said steam chamber.

9. An apparatus for determining quantities of enthalpy of a dry steam medium, comprising tubular duct means connected to a steam chamber through which the medium is passed; dosing means in said duct means to control the amount of the steam medium passing out of said chamber; cooling means for altering a thermal condition of the passing medium; at least one means for measuring temperatures of the passing medium; heat flow measuring means installed between said duct means and said cooling means; said heat flow measuring means including two concentric electrically insulated wire coils of a material having temperature dependent resistance, said coils being disposed around said duct means in spaced and concentric relationship to each other, and further including a layer of a material of a moderate thermal conductivity and having a predetermined thickness, said layer being interposed between the two wire coils to form a thermal resistance, said coils arranged at opposite sides of the thermal resistance to determine the heat flow as a function of temperature difference across said resistance; and collecting means arranged at the outlet of said duct means; whereby the quantities of enthalpy are computed from a heat balance equation which is set up from the measured data of mass flow, heat flow and temperature.

* * * * *